United States Patent
Kubota et al.

(10) Patent No.: US 11,213,463 B2
(45) Date of Patent: Jan. 4, 2022

(54) OIL-IN-WATER TYPE COSMETIC COMPOSITION

(71) Applicant: SHISEIDO COMPANY, LTD., Tokyo (JP)

(72) Inventors: Shun Kubota, Yokohama (JP); Hideo Hata, Yokohama (JP); Malyn Concina, East Windsor, NJ (US); Michelle Lou, East Windsor, NJ (US); Hideki Takahashi, Yokohama (JP); Julie Shown, San Francisco, CA (US); Yosuke Ikebe, San Francisco, CA (US)

(73) Assignee: SHISEIDO COMPANY, LTD., Tokyo (JP)

( * ) Notice: Subject to any disclaimer, the term of this patent is extended or adjusted under 35 U.S.C. 154(b) by 432 days.

(21) Appl. No.: 15/206,639

(22) Filed: Jul. 11, 2016

(65) Prior Publication Data

US 2017/0007512 A1    Jan. 12, 2017

Related U.S. Application Data

(60) Provisional application No. 62/190,348, filed on Jul. 9, 2015.

(51) Int. Cl.
*A61K 8/06* (2006.01)
*A61K 8/31* (2006.01)
*A61Q 1/02* (2006.01)
*A61K 8/29* (2006.01)
*A61K 8/36* (2006.01)
*A61K 8/49* (2006.01)
*A61Q 17/04* (2006.01)
*A61K 8/02* (2006.01)

(52) U.S. Cl.
CPC .......... *A61K 8/062* (2013.01); *A61K 8/0241* (2013.01); *A61K 8/29* (2013.01); *A61K 8/31* (2013.01); *A61K 8/361* (2013.01); *A61K 8/4973* (2013.01); *A61Q 1/02* (2013.01); *A61Q 17/04* (2013.01); *A61K 2800/34* (2013.01); *A61K 2800/43* (2013.01); *A61K 2800/5922* (2013.01); *A61K 2800/612* (2013.01)

(58) Field of Classification Search
None
See application file for complete search history.

(56) References Cited

U.S. PATENT DOCUMENTS

2011/0236447 A1* 9/2011 Yoshimura .............. A61K 8/06
424/401

FOREIGN PATENT DOCUMENTS

| EP | 0036199 B1 * | 7/1984 | ............... A61K 8/11 |
|---|---|---|---|
| JP | 58-62106 | 4/1983 | |
| JP | 2003-95850 | 4/2003 | |
| JP | 2006-232712 | 9/2006 | |
| JP | 2009203200 | 9/2009 | |
| JP | 528139 | 7/2013 | |
| JP | 5228139 | 7/2013 | |
| JP | WO 2017/006488 | 12/2017 | |
| WO | WO-2013118836 A1 * | 8/2013 | ............... A61K 8/31 |

OTHER PUBLICATIONS

Vet Way. Liquid Paraffin MSDS. <http://www.vamerpharma.com/HCP/liquid%20paraffin%20safety%20datasheet.pdf.>Available Aug. 15, 2003; accessed Oct. 12, 2017 (Year: 2003).*
The Good Scents Company. Isodecyl Neopentanoate. http://www.thegoodscentscompany.com/data/rw1301311.html.>Available Nov. 3, 2009; accessed Oct. 13, 2017 (Year: 2009).*
Cecchini and Issberner "Silicone Alternatives in Personal Care". < https://www.happi.com/issues/2010-11/view_features/silicone-alternatives-in-personal-care/> available Nov. 2010; accessed Oct. 13, 2017 (Year: 2010).*
Kohler et al. "Colour chart: Establishing the causes of colouring in iron oxide pigments" European Coatings Journal. Jan. 2014 < http://bayferrox.com/uploads/tx_lxsmatrix/ecj_2014_01_koehler.pdf> (Year: 2014).*
English translation of WO 2013/118836 A1 (Year: 2012).*
PCT/JP2015/070736 (WO 2017/006488), International Search Report (2-pages Japanese, 2-pages English) and Written Opinion (4 pages—Englisy), dated Oct. 20, 2015.

* cited by examiner

*Primary Examiner* — Nicole P Babson
(74) *Attorney, Agent, or Firm* — Andrew F. Young; Nolte Lackenbach Siegel

(57) ABSTRACT

An oil-in-water type emulsified cosmetic and a method of making can be prepared in a system not containing a silicone and is surprisingly produced without a wet-type dispersion apparatus by using a specific combination of the oil component constituting the oily phase and a hydrophobizing agent for a hydrophobized powder. The composition includes an aqueous phase; an oily phase dispersed in the aqueous phase; and a powder dispersed in the oily phase. The oily phase comprises (a) volatile hydrocarbon oil and (b) non-volatile hydrocarbon oil in a combined amount of 40% by mass or more with respect to the total oil content, wherein the blending ratio of (b) non-volatile hydrocarbon oil to (a) volatile hydrocarbon oil, [(b)/(a)], is within a range of 0 to 2.5, and the powder comprises a powder having a surface hydrophobized by a treatment with a metallic soap consisting of a higher fatty acid and a divalent metal or a composite treatment with a higher fatty acid and a divalent metal hydroxide.

15 Claims, No Drawings

OIL-IN-WATER TYPE COSMETIC COMPOSITION

CROSS REFERENCE TO RELATED APPLICATIONS

This application relates to and claims priority from U.S. Prov. Ser. No. 62/190,348 filed Jul. 9, 2015, the entire contents of which are incorporated herein by reference.

FIGURE SELECTED FOR PUBLICATION

None.

BACKGROUND OF THE INVENTION

The present invention relates to an oil-in-water type emulsified cosmetic, wherein a powder is evenly dispersed in an internal oily phase. More specifically, the invention relates to an oil-in-water type emulsified cosmetic that is easily produced while also excelling in stability and dispersibility of the powder.

BACKGROUND ART

Oil-in-water type emulsified cosmetics containing titanium dioxide and zinc oxide are known. In particular, oil-in-water type emulsified cosmetics, wherein a hydrophobized powder is dispersed in an oily phase, have a watery and refreshing feeling of use, and also have excellent properties such as makeup durability after application.

In emulsion systems having a powder dispersed in an oily phase, there is a problem in how to obtain stability and uniform dispersibility of the powder. Conventionally, there is a requirement to produce the emulsion by mechanically dispersing the hydrophobized powder in the oily phase using a powerful wet-type dispersion apparatus such as a bead mill or a ball mill.

With the above-described production method, there have been attempts to improve the emulsion stability and dispersibility of the powder by blending in specific dispersants or emulsifying agents (Patent Document 1), or thickening the external phase (aqueous phase) (Patent Document 2), and unfortunately these have yielded only a certain degree of effects and are not satisfactory.

On the other hand, while conventional oil-in-water type emulsified cosmetics have a powder dispersed in an oily phase usually contain a silicone oil as an oily phase component, recent trends towards a more naturally-oriented outlook have led to consumers desiring cosmetics not containing silicone oils (non-silicone cosmetics). However, it is clearly not known that there are examples of production of oil-in-water type emulsified cosmetics having a powder dispersed in an oily phase in a system not containing a silicone oil.

RELATED ART DOCUMENTS

Patent Documents

[Patent Document 1] JP 5228139 B
[Patent Document 2] JP 5053887 B

ASPECTS AND SUMMARY OF THE INVENTION

Reference will now be made in detail to embodiments of the invention. It will also be understood that other embodiments may be utilized without departing from the scope of the present invention, and that the detailed description is not to be taken in a limiting sense or otherwise noted as in the appended claims without requirements of the written description being required thereto. It will also be recognized that the disclosed compositions and processes may be understood as methods of preparation or methods of preparing the same without departing from the scope and spirit of the present invention and that various operations in simplified form may be described as multiple discrete operations in turn, or in a manner that may be helpful in understanding embodiments of the present invention; however, the order of description should not be construed to imply that these operations are order dependent.

Problems to be Solved by the Invention

The present invention was made in view of the aforementioned circumstances, and addresses the problem of providing an oil-in-water type emulsified cosmetic that can be prepared even in a system not containing a silicone and that can be easily produced without using a powerful wet-type dispersion apparatus such as a bead mill.

Means for Solving the Problems

As a result of performing diligent research, the present inventors discovered that the aforementioned problems could be solved by using a specific combination of the oil component constituting the oily phase and the hydrophobizing agent for the hydrophobized powder, thereby achieving the present invention.

In other words, the present invention relates to an oil-in-water type emulsified cosmetic composition comprising an aqueous phase; an oily phase dispersed in the aqueous phase; and a powder dispersed in the oily phase; wherein the oily phase comprises (a) volatile hydrocarbon oil and (b) non-volatile hydrocarbon oil in a combined amount of 40% by mass or more with respect to the total oil content, wherein the blending ratio of (b) non-volatile hydrocarbon oil to (a) volatile hydrocarbon oil, [(b)/(a)], is within a range of 0 to 2.5, and wherein the powder comprises a powder having a surface hydrophobized by a treatment with a metallic soap consisting of a higher fatty acid and a divalent metal or a composite treatment with a higher fatty acid and a divalent metal hydroxide.

Effects of the Invention

The oil-in-water type emulsified cosmetic of the present invention is capable of evenly and stably dispersing a hydrophobized powder in an oily phase under mild conditions using a homo mixer or the like, and the oil-in-water type emulsified cosmetic obtained by emulsifying the resulting oily phase in an aqueous phase excels in stability and provides a refreshing sensation of use. Additionally, it can be prepared in a system not containing a silicone.

BRIEF DESCRIPTION OF THE DRAWINGS

None.

DETAILED DESCRIPTION OF THE PREFERRED EMBODIMENTS

Modes for Carrying Out the Invention

The cosmetic according to the present invention is an oil-in-water type emulsified cosmetic wherein an internal oily phase is dispersed in an external aqueous phase, and a powder is dispersed in the oily phase.

The oily phase in the oil-in-water type emulsified cosmetic of the present invention comprises (a) volatile hydrocarbon oil and (b) non-volatile hydrocarbon oil, such that the content ratio [(b)/(a)] between the (a) volatile hydrocarbon oil and the (b) non-volatile hydrocarbon oil is in the range of 0 to 2.5. In other words, the cosmetic of the present invention includes modes wherein (b) non-volatile hydrocarbon oil is not contained in the oily phase, while on the other hand, when containing (b) non-volatile hydrocarbon oil, its content ratio [(b)/(a)] with respect to (a) volatile hydrocarbon oil should be 2.5 or lower, preferably 2.0 or lower, more preferably 1.5 or lower, and even more preferably 1.0 or lower.

The (a) volatile hydrocarbon oil in the present invention refers to a hydrocarbon oil having a boiling point lower than 300° C. at 1 atm, specific examples of which include light isoparaffins, isododecane and isohexadecane.

The (b) non-volatile hydrocarbon oil in the present invention refers to a hydrocarbon oil having a boiling point of 300° C. or higher at 1 atm, examples of which include squalane, hydrogenated polydecene and a petrolatum such as that marketed under the trade name VASELINE®.

In the cosmetic of the present invention, the combined amount of the (a) volatile hydrocarbon oil and the (b) non-volatile hydrocarbon oil must be at least 40 mass % with respect to the total oil content. The combined amount of the (a) volatile hydrocarbon oil and the (b) non-volatile hydrocarbon oil may, for example, be at least 50 mass %, at least 0 mass %, at least 70 mass %, at least 80 mass %, or at least 85 mass %, and the upper limit is not particularly limited, but may be at most 100 mass %, at most 95 mass %, or at most 90 mass %.

The oily phase in the cosmetic of the present invention may contain arbitrary oil components other than the (a) volatile hydrocarbon oil and the (b) non-volatile hydrocarbon oil, such as oils/fats, waxes, higher fatty acids, higher alcohols, ester oils or the like, within a range not compromising the effects of the present invention.

Examples of the arbitrary oil component include isopropyl myristate, octyldodecyl myristate, isopropyl palmitate, butyl stearate, hexyl laurate, myristyl myristate, decyl oleate, hexyldecyl dimethyloctanote, cetyl lactate, myristyl lactate, lanolin acetate, isocetyl stearate, isocetyl isostearate, cholesteryl 12-hydroxystearate, ethylene glycol di-2-ethylhexonate, dipentaerythritol fatty acid ester, N-alkylglycol monoisostearate, neopentyl glycol dicaprate, diisostearyl malate, glycerin di-2-heptylundecanoate, trimethylolpropane tri-2-ethylhexanoate, pentaerythritol tetra-2-ethylhexanoate, glycerin tri-2-ethylhexanoate, trimethylolpropane triisostearate, cetyl 2-ethylhexanoate, 2-ethylhexyl palmitate, glycerin trimyristate, glyceryl tri(caprylate/caprate), triethylhexanoin, cetyl ethylhexanoate, polyglyceryl-2 triisostearate, dipentaerythrityl hexahydroxystearate, pentaerythrityl tetra(behenate/benzoatekthylhexanoate), PPG-3 dipivalate, dipentaerythrityl tripolyhydroxystearate, pentarythrityl tetra(ethylhexanoate/benzoate), macadamia nut oil polygylceryl-6 esters behenate, (phytosteryl/behenyl) dimer dilinoleate, lanolin, diethylhexyl succinate, octyldodecyl lanolin fatty acid, isostearyl palmitate, diheptylundecyl adipate, isocetyl myristate, dihexyldecyl adipate, diisopropyl sebacate, pentaerythrityl tetraethylhexanoate, tri-2-heptylundecanoic acid glyceride, castor oil fatty acid methyl ester, oleyl oleate, cetostearyl alcohol, acetoglyceride, 2-heptylundecyl palmitate, diisobutyl adipate, 2-octyldodecyl N-lauroyl-L-glutamate, di-2-heptyundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate, triethyl citrate, avocado oil, Japanese camellia oil, turtle oil, macadamia nut oil, corn oil, mink oil, olive oil, rapeseed oil, egg yolk oil, sesame seed oil, persic oil, wheat germ oil, sasanqua oil, castor oil, flaxseed oil, safflower oil, cottonseed oil, perilla oil, soybean oil, peanut oil, tea seed oil, torreya seed oil, rice bran oil, paulownia oil, jojoba oil, germ oil, triglycerin, glycerin trioctanoate and glycerin triisopalmitate.

The amount of the oil component in the cosmetic of the present invention is preferably 1 to 40 mass %, more preferably 5% to 30% with respect to the total amount of the cosmetic.

The cosmetic of the present invention essentially contains (a) volatile hydrocarbon oil as the oil component, and optionally contains (b) non-volatile hydrocarbon oil, these hydrocarbon oils occupying a significant portion of the oil component. Additionally, the powder in the oily phase is evenly and conveniently dispersed by performing the below-described specific treatments as the surface treatment of the powder to be dispersed. Therefore, there is no need to add a volatile silicone oil for the purpose of lightening the sensation of use as in conventional cosmetics. Therefore, the cosmetic of the present invention can be formulated as a so-called non-silicone cosmetic that does not contain a silicone oil.

In the cosmetic of the present invention, the powder is dispersed in the oily phase. The powder is not particularly limited, and for example, includes titanium dioxide, iron oxide and zinc oxide subjected to a specific hydrophobization treatment.

The specific hydrophobization treatment in the present invention refers to (1) a treatment with a metallic soap consisting of a higher fatty acid and a divalent metal, or (2) a composite treatment with a higher fatty acid and a divalent metal hydroxide. The higher fatty acid used in this case is preferably a C8 to C24 (preferably C12 to C22) linear or branched carboxylic acid. Specific examples include stearic acid and isostearic acid. As the divalent metal, magnesium is particularly preferred.

The hydrophobization treatment method is not particularly limited, and a wet method using a solvent, a vapor phase method, or a mechanochemical method can be used.

The aforementioned powder subjected to a specific hydrophobization treatment is one or more selected from the group consisting of pigment-grade titanium dioxide, fine particle titanium dioxide, pigment-grade zinc oxide, fine particle zinc oxide, talc, mica, sericite, kaolin, titanated mica, black iron oxide, yellow iron oxide, red iron oxide, ultramarine, Prussian blue, chromium oxide, chromium hydroxide, silica and cerium oxide. In general, powders having a smaller particle size are capable of more easily being dispersed, so conventionally, they were dispersed while mechanically pulverizing the powders using a wet-type dispersion apparatus such as a bead mill. However, in the cosmetic of the present invention, even if the aforementioned titanium dioxide or zinc oxide that has been subjected to a specific surface treatment is a powder having a large size, such as pigment grade (average particle size about 0.2 to 0.4 μm), it can be easily dispersed in an oily phase containing a hydrocarbon oil. Therefore, particularly in the case of including a powder having relatively large particle size, such as pigment-grade titanium dioxide or zinc oxide, the advantageous characteristics of the present invention can be achieved.

The powder contained in the cosmetic of the present invention may, in addition to the aforementioned powder that has been subjected to a specific hydrophobization treatment, include an optional powder that is normally capable of being blended into cosmetics.

The aforementioned optional powder can be an untreated powder, or a powder that has been subjected to a surface hydrophobization treatment (other than the specified hydrophobization treatment).

While the average particle size of the powder is not particularly limited, a powder having an average primary particle size of 0.001 μm to 100 μm, preferably 0.001 μm to 10 μm should be used. However, the average particle size should preferably be adjusted so as to be smaller than the emulsified particles in the oily phase.

The powder content in the cosmetic of the present invention can be appropriately chosen based on the desired product form. For example, in the case of a base cosmetic or foundation, it should preferably be 8 to 60 mass %, and in the case of a sunscreen cosmetic, it should preferably be 10 to 35 mass %.

The aqueous phase in the oil-in-water type emulsified cosmetic of the present invention should preferably contain a thickener. By including a thickener, the stability of the emulsion is further improved.

The thickener may be of one or more types selected from the group consisting of natural or synthetic thickeners that can be contained in cosmetics. Specific examples include succinoglycan, xanthan gum, carrageenan, gellan gum, starch, hydroxyalkylcellulose, pullulan, carbomer, (Na/Mg) silicate, bentonite, acrylamide copolymer, sodium acryloyl dimethyl taurine/hydroxyethyl acrylate copolymer, agar, polyurethane, and hydrophobic polyether polyurethane. Among these, naturally occurring thickeners such as agar, sugars or derivatives thereof are preferable used. Additionally, a microgel such as that described in JP 2001-342451 A, a published document, the entire contents of which are incorporated herein by reference, is also preferable.

The thickener content in the cosmetic of the present invention should preferably be 0.1 to 3 mass % with respect to the total amount of the cosmetic. If the thickener content is too low, the improvement in stability may not be sufficient, and if the content is too high, the sensation of use may be worsened due to clumping.

Furthermore, the aqueous phase preferably contains one or more emulsifying agents selected from the group consisting of carboxymethylcellulose, hydroxyethylcellulose, hydroxymethylcellulose, hydroxypropylcellulose and gelatin.

Additionally, components that are normally contained in cosmetics, for example, UV absorbing agents, humectants, fragrances, surfactants, various pharmaceutically effective components, preservatives and antioxidants can be added in accordance with need, within a range not compromising the effects of the present invention.

Unlike with conventional production methods, the cosmetic of the present invention can be conveniently produced under mild conditions. For example, it can be produced by dispersing the powder among the oily phase components by means of a homo mixer or the like, adding the resulting oily phase to the aqueous phase using a homo mixer or the like, stirring and emulsifying.

The oil-in-water type emulsified cosmetic of the present invention can be provided as a base cosmetic, a foundation or a sunscreen cosmetic.

EXAMPLES

Here below, the present invention will be explained in further detail with reference to examples, but the present invention is not limited by these examples. Where not otherwise indicated, amounts are provided in mass %.

Oil-in-water type emulsified cosmetics (samples) were prepared with the formulations shown in the below-indicated Table 1. A sample of each example was evaluated according to the following categories. The results are shown together in Table 1.

(1) Emulsion Stability (Powder Dispersability)

Observations were made by an eye as to the presence or absence of color irregularities caused by powder granules or powder agglomeration when the samples were applied to a black plate.

A+: absolutely no powder color irregularities caused by powder granules or agglomeration when applied to a plate were observed A−: slight powder color irregularities caused by extremely small powder granules or agglomeration when applied to a plate were observed B: powder color irregularities caused by small powder granules or agglomeration when applied to a plate were observed (not presenting problems for use)

C: color irregularities caused by relatively large powder granules or agglomeration when applied to a plate were observed (2) Evenness of Finish Female panelists (10 subjects) evaluated a sample of each example and comparative example regarding the evenness of finish after application, on the basis of the following evaluation criteria.

(Evaluation)

A+: 8 or more replied that they felt an evenness of finish
A−: 6 or 7 replied that they felt an evenness of finish
B: 3 to 5 replied that they felt an evenness of finish
C: 2 replied that they felt an evenness of finish (3) Smoothness of Spreading Female panelists (10 subjects) evaluated a sample of each example and comparative example regarding the smoothness of spreading during application, on the basis of the following evaluation criteria.

(Evaluation)

A+: 8 or more replied that they felt a smoothness of spreading
A−: 6 or 7 replied that they felt a smoothness of spreading
B: 3 to 5 replied that they felt a smoothness of spreading
C: 2 replied that they felt a smoothness of spreading

TABLE 1

|  | Ex. 1 | Ex. 2 | Ex. 3 | Ex. 4 | Comp. Ex. 1 | Comp. Ex. 2 |
| --- | --- | --- | --- | --- | --- | --- |
| Ion exchanged water | balance | balance | balance | balance | balance | balance |
| Sorbitan sesquiisostearate | 0.5 | 0.5 | 0.5 | 0.5 | 0.5 | 0.5 |
| Isostearic acid | 1 | 1 | 1 | 1 | 1 | — |
| (b) Squalane | — | 6 | 9.575 | 13.15 | 19.15 | 6 |
| (a) Isododecane | 19.15 | 13.15 | 9.575 | 6 | — | 13.15 |

TABLE 1-continued

|  | Ex. 1 | Ex. 2 | Ex. 3 | Ex. 4 | Comp. Ex. 1 | Comp. Ex. 2 |
| --- | --- | --- | --- | --- | --- | --- |
| Hydrophobized fine particle titanium dioxide (*1) | 7.5 | 7.5 | 7.5 | 7.5 | 7.5 | — |
| Hydrophobized fine particle titanium dioxide (*2) | — | — | — | — | — | 7.5 |
| Hydrophobized pigment grade titanium dioxide (*3) | 3.2 | 3.2 | 3.2 | 3.2 | 3.2 | — |
| Hydrophobized pigment grade titanium dioxide (*4) | — | — | — | — | — | 3.2 |
| Yellow iron oxide | 1.1 | 1.1 | 1.1 | 1.1 | 1.1 | 1.1 |
| Red iron oxide | 0.2 | 0.2 | 0.2 | 0.2 | 0.2 | 0.2 |
| Black iron oxide | 0.04 | 0.04 | 0.04 | 0.04 | 0.04 | 0.04 |
| Silica | 2 | 2 | 2 | 2 | 2 | 2 |
| Total | 100 | 100 | 100 | 100 | 100 | 100 |
| Content ratio [(b)/(a)] | 0 | 0.46 | 1 | 2.2 | ∞ | 0.46 |
| Emulsion stability (powder dispersibility) | A+ | A+ | A− | B | B | C |
| Evenness of finish | B | A+ | A− | B | C | C |
| Smoothness of spreading | A+ | A+ | A+ | A+ | A+ | B |

(*1) Composite treatment with isostearic acid and magnesium hydroxide
(*2) Silicone treatment
(*3) Magnesium isostearate treatment
(*4) Silicone treatment As is clear from the results shown in Table 1, Examples 1 to 4 wherein the blending ratio [(b)/(a)] of (b) non-volatile hydrocarbon oil to (a) volatile hydrocarbon oil contained in the oily phase is within the range of 0 to 2.5 and containing titanium dioxide subjected to the specific surface hydrophobization treatment of the present application were satisfactory in terms of all of the evaluated categories. In surprising contrast, Comparative Example 1 not containing volatile hydrocarbon oil did not have an even finish, and also in surprising contrast in Comparative Example 2 containing titanium dioxide surface-treated with silicone, the powder was not evenly dispersed and the finish was inferior.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An oil-in-water type emulsified cosmetic composition, comprising:
   an aqueous phase;
   1 to 40% by mass of an oily phase dispersed in the aqueous phase; and
   a powder dispersed in the oily phase;
wherein the oily phase comprises:
   (a) volatile hydrocarbon oil and
   (b) non-volatile hydrocarbon oil
in a combined amount of 40% by mass or more with respect to the total oil content;
wherein the blending ratio of said (b) non-volatile hydrocarbon oil to said (a) volatile hydrocarbon oil, [(b)/(a)], is within the range of 0.10 to 2.5; and
wherein the powder has a surface hydrophobized by a treatment with a metallic soap consisting of a higher fatty acid and a divalent metal, or by a composite treatment with a higher fatty acid and a divalent metal hydroxide.

2. The cosmetic composition according to claim 1, further comprising:
   a thickener in the aqueous phase.

3. The cosmetic composition according to claim 2, wherein:
   the thickener is one or more selected from the group consisting of succinoglycan, xanthan gum, carrageenan, gellan gum, starch, hydroxyalkylcellulose, pullulan, carbomer, (Na/Mg) silicate, bentonite, acrylamide copolymer, sodium acryloyl dimethyl taurine/hydroxyethyl acrylate copolymer, agar, polyurethane, and hydrophobic polyether polyurethane.

4. The cosmetic composition according to claim 1, wherein:
   the powder is one or more selected from the group consisting of: titanium dioxide, iron oxide and zinc oxide.

5. The cosmetic composition according to claim 4, wherein:
   the powder is a pigment grade powder.

6. The cosmetic composition according to claim 1, wherein:
   the higher fatty acid is a C8 to C24 fatty acid, and the divalent metal is magnesium.

7. The cosmetic composition according to claim 6, wherein:
   the higher fatty acid is a C12 to C22 linear or branched carboxylic acid.

8. The cosmetic composition, according to claim 1, wherein:
   said composition is absent a silicone oil.

9. The cosmetic composition, according to claim 5, wherein:
   the composition further comprises: a microparticle powder selected from the group consisting of titanium dioxide microparticles, iron oxide microparticles and zinc oxide microparticles.

10. An oil-in-water type emulsified cosmetic composition, comprising:
    an aqueous phase;
    10 to 40% by mass of an oily phase dispersed in the aqueous phase; and a powder dispersed in the oily phase;
wherein the oily phase does not include a silicone oil and further comprises:
(a) volatile hydrocarbon oil and
(b) non-volatile hydrocarbon oil
in a combined amount of 40% by mass or more with respect to the total oil content; and
wherein the blending ratio of (b) non-volatile hydrocarbon oil to (a) volatile hydrocarbon oil, [(b)/(a)], is within the range of 0.10 to 2.5; and
wherein the powder has a surface hydrophobized by a treatment with a metallic soap consisting of a higher fatty acid and a divalent metal, or by a composite treatment with a higher fatty acid and a divalent metal hydroxide.

11. The cosmetic composition, according to claim 10, wherein:
the powder comprises: a pigment-grade powder selected from the group consisting of titanium dioxide, iron oxide and zinc oxide; and
the composition further comprises a microparticle powder selected from the group consisting of titanium dioxide microparticles, iron oxide microparticles and zinc oxide microparticles.

12. An oil-in-water type emulsified cosmetic composition comprising:
an aqueous phase;
1 to 40% by mass of an oily phase dispersed in the aqueous phase; and
a powder dispersed in the oily phase;
wherein the oily phase comprises:
(a) volatile hydrocarbon oil and
(b) non-volatile hydrocarbon oil
in a combined amount of 40% by mass or more with respect to the total oil content, and does not include a silicone oil;
wherein the blending ratio of (b) non-volatile hydrocarbon oil to (a) volatile hydrocarbon oil, [(b)/(a)], is within the range of 0.10 to 2.5; and
wherein:
the powder has a surface hydrophobized by a treatment with a metallic soap consisting of a higher fatty acid and a divalent metal, or by a composite treatment with a higher fatty acid and a divalent metal hydroxide;
the powder comprises a pigment-grade powder selected from the group consisting of titanium dioxide, iron oxide and zinc oxide; and
the composition further comprises a microparticle powder selected from the group consisting of titanium dioxide microparticles, iron oxide microparticles and zinc oxide microparticles.

13. The cosmetic composition according to claim 1, wherein:
(a) the volatile hydrocarbon oil is selected from the group consisting of light isoparaffin, isododecane and iso-hexadecane; and
(b) the non-volatile hydrocarbon oil is selected from the group consisting of squalane, hydrogenated polydecene and petrolatum.

14. The cosmetic composition according to claim 10, wherein:
(a) the volatile hydrocarbon oil is selected from the group consisting of light isoparaffin, isododecane and iso-hexadecane; and
(b) the non-volatile hydrocarbon oil is selected from the group consisting of squalane, hydrogenated polydecene and petrolatum.

15. The cosmetic composition according to claim 12, wherein:
(a) the volatile hydrocarbon oil is selected from the group consisting of light isoparaffin, isododecane and iso-hexadecane; and
(b) the non-volatile hydrocarbon oil is selected from the group consisting of squalane, hydrogenated polydecene and petrolatum.

* * * * *